United States Patent [19]

Mueller

[11] 3,989,719
[45] Nov. 2, 1976

[54] DIBENZOXAZEPINE N-CARBOXYLIC ACID HYDRAZIDES AND DERIVATIVES

[75] Inventor: Richard A. Mueller, Glencoe, Ill.

[73] Assignee: G. D. Searle & Co., Chicago, Ill.

[22] Filed: Feb. 5, 1973

[21] Appl. No.: 329,406

Related U.S. Application Data

[63] Continuation-in-part of Ser. No. 127,360, March 23, 1971, abandoned.

[52] U.S. Cl. ............................... 260/333; 424/244
[51] Int. Cl.² ...................................... C07D 267/20
[58] Field of Search .................................. 260/333

[56] References Cited
UNITED STATES PATENTS 3,534,019  10/1970  Coyne et al. .................... 260/239

OTHER PUBLICATIONS

William E. Coyne et al., Jour. Med. Chem., 11 (6), (1968), pp. 1158–1160.

J. H. Sanner, Arch. int. Pharmacodyn., July 1969, No. 1, pp. 46–56.

*Primary Examiner*—Norma S. Milestone
*Attorney, Agent, or Firm*—John A. Dhuey

[57] ABSTRACT

Derivatives of the dibenzoxazepine N-carboxylic acid hydrazides are acylated to yield N,N'-diacyl hydrazines which are useful pharmacological agents as is evidenced by their acetylcholine antagonist, prostaglandin antagonist, and 5-hydroxytryptamine antagonist activity.

4 Claims, No Drawings

DIBENZOXAZEPINE N-CARBOXYLIC ACID HYDRAZIDES AND DERIVATIVES

This application is a continuation-in-part of my copending application Ser. No. 127,360, filed Mar. 23, 1971 and now abandoned.

This invention is concerned generally with derivatives of the dibenzoxazepine N-carboxylic acid hydrazides and more specifically with compounds of the following general formula

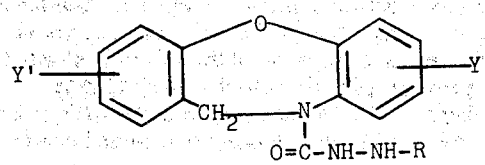

wherein Y and Y' are hydrogen, halogen, methyl or trifluoromethyl and R is a higher alkanoyl radical. The higher alkanoyl radicals represented by the above formula are those comprised of 7 to 12 carbon atoms and are illustrated by heptanoyl, octanoyl, nonanoyl and the corresponding branched-chain isomers. The halogen radicals intended are chlorine, iodine, bromine, and fluorine.

A most preferred method of producing the instant compounds of the present invention involves optionally substituted dibenzoxazepine N-carboxylic acid hydrazides as starting materials. The preparation of these compounds is disclosed in U.S. Pat. No. 3,534,019.

Acylation of the aforementioned hydrazides with the appropriate acylating agent in an inert medium, preferably in the presence of an acid acceptor, affords the desired N,N'-diacyl hydrazines. The acid chlorides and acid anhydrides are most preferred acylating agents. Preferred acid acceptors are triethylamine, potassium carbonate, sodium bicarbonate, and sodium carbonate, and convenient solvents are benzene-methylene chloride and acetonitrile.

The reaction of an alkanoyl halide and the hydrazide is illustrated by contacting 8-chloro-10,11-dihydrodibenz-[b,f][1,4]oxazepine-10-carboxylic acid hydrazide with octanoyl chloride in the presence of sodium bicarbonate to give 1-octanoyl-2-(8-chloro-10,11-dihydrodibenz[b,f][1,4]oxazepine-10-carbonyl)hydrazine.

Also, the compounds of the present invention may be prepared by treating the dibenzoxazepine carbonyl chloride in a basic medium with the appropriate acyl hydrazide. This method is particularly convenient when the alkanoyl chlorides are difficult to prepare.

The novel compounds of this invention are valuable pharmacological agents. They are active prostaglandin, 5-hydroxytryptamine and acetylcholine antagonists. In addition they are useful as topical anti-inflammatory, anti-diarrheal and anti-sebum agents. They possess greater potency than previously disclosed compounds and also exhibit minimal undesirable effects upon the central nervous system, e.g. analgesic and anti-convulsant.

The prostaglandin, acetylcholine, and 5-hydroxytryptamine antagonist activity is demonstrated in the following procedure which is substantially the same as that described by J. H. Sanner, Arch. int. Pharmacodyn., 180 (1), 46 (1969):

Female albino guinea pigs weighing 200–500 g. are sacrificed by cervical dislocation and the ileum is quickly removed and placed in modified Tyrode solution containing one-half the usual amount of magnesium ions. Segments of ileum, about 2 centimeters long are cut and mounted in a 2 or 4 ml. tissue bath containing the modified Tyrode solution. The solution is maintained at 37° and bubbled with a gaseous mixture of 95% oxygen and 5% carbon dioxide. Contractions are detected isotonically. Approximately equal submaximal contractions are obtained in preliminary trials by adjusting the doses of prostaglandin $E_2$ ($PGE_2$), 5-hydroxytryptamine, and acetylcholine added to the bath. Two control contractions are obtained at 3.5 minute intervals. A solution or suspension of the test compound in the bathing solution is then substituted for the original modified Tyrode solution. The test suspension is kept in constant contact with the tissue for the remainder of the experiment except for brief periods to drain the bath in preparation for rinsing with fresh test suspension. Three more contractions are elicited to each agonist in the presence of the test compound without interrupting the time sequence. The last two sets of treated responses are compared with the two sets of control responses. The first set of treated responses is not used for comparisons, being used only to maintain the timed sequence of injections during the period allowed for the tissue to become equilibrated with the antagonist. A compound is rated active if the mean of contractions produced by any agonist is reduced 75% or more by the test compound.

The following examples will further illustrate the present invention. They should not be construed as limiting the invention either in spirit or in scope as modifications both in materials and methods will be apparent to those skilled in the art. In these examples temperatures are indicated in degrees Centigrade (°C.) and quantities of materials in parts by weight unless parts by volume is specifically expressed.

EXAMPLE 1

To a solution of 0.5 part of 8-chloro-10,11-dihydrodibenz[b,f][1,4]oxazepine-10-carboxylic acid hydrazide and 19.6 parts of acetonitrile is added 0.298 part of sodium bicarbonate followed by 0.562 part of octanoyl chloride. The solution is stirred for 48 hours at room temperature, after which time the solvent is removed under reduced pressure and the resulting oil crystallized by trituration with cyclohexane. Recrystallization from cyclohexane yields 1-octanoyl-2-(8-chloro-10,11-dihydrodibenz[b,f][1,4]oxazepine-10-carbonyl) hydrazine, melting at about 127°–129° and represented by the following structural formula

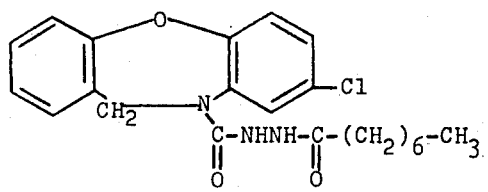

EXAMPLE 2

Substitution of equivalent quantities of potassium carbonate and heptanoyl chloride in the procedure of Example 1 affords 1-heptanoyl-2-(8-chloro-10,11-dihydrodibenz[b,f][1,4]oxazepine-10-carbonyl) hydrazine, melting at about 131°–132°. The following structural formula represents this compound

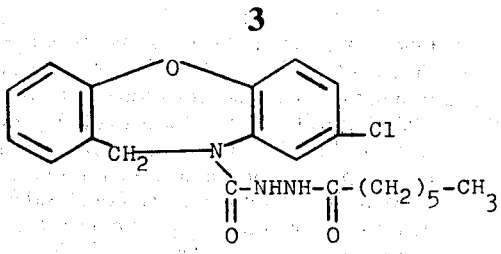

EXAMPLE 3

By substituting equivalent quantities of 8-trifluoromethyl-10,11-dihydrodibenz[b,f][1,4]oxazepine-10-carboxylic acid hydrazide, sodium carbonate and octanoyl chloride in the procedure of Example 1, there is obtained 1-octanoyl-2-(8-trifluoromethyl-10,11-dihydrodibenz[b,f][1,4]oxazepine-10-carbonyl)hydrazine, which melts at about 97°–100° and is represented by the following structural formula

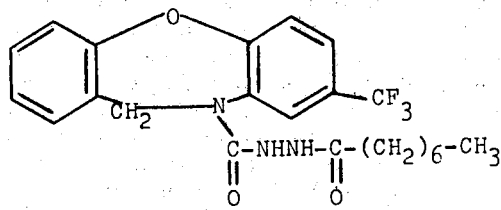

EXAMPLE 4

The substitution of equivalent quantities of 8-chloro-10,11-dihydrodibenz[b,f][1,4]oxazepine-10-carboxylic acid hydrazide, sodium carbonate and decanoyl chloride in the procedure of Example 1 results in 1-decanoyl-2-(8-chloro-10,11-dihydrodibenz[b,f][1,-4]oxazepine-10-carbonyl)hydrazine, which compound is represented by the following structural formula

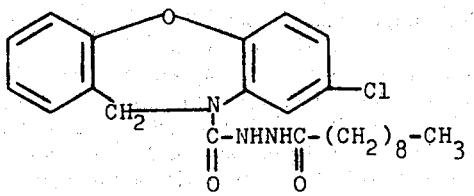

EXAMPLE 5

To a solution containing 2.9 parts of 8-chloro-10,11-dihydrodibenz[b,f][1,4]oxazepine-10-carboxylic acid hydrazide, 50 parts by volume of acetonitrile and excess aqueous potassium carbonate is added 1.6 parts of 3-cyclopentylpropionyl chloride and the resulting reaction mixture is stirred at room temperature for about 2 days. The solvent is stripped under reduced pressure and the resulting residue is purified by chromatography on a silica gel column, using ethyl acetate-benzene solutions as the eluants. The 5% ethyl acetate in benzene eluate, after removal of the solvents, affords 1-(3-cyclopentylpropionyl)-2-(8-chloro-10,11-dihydrodibenz[b,f][1,4]oxazepine-10-carbonyl)hydrazine, characterized by the following structural formula

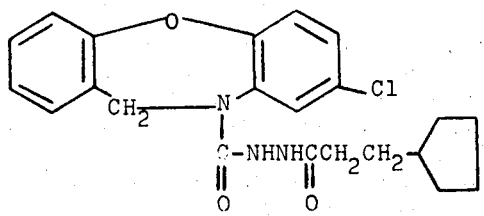

What is claimed is:
1. A compound of the formula

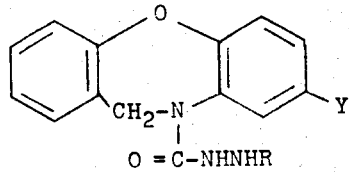

wherein Y is a chloro radical and R is an alkanoyl radical containing 7–12 carbon atoms.

2. As in claim 1, the compound which is 1-octanoyl-2-(8-chloro-10,11-dihydrodibenz[b,f][1,4]oxazepine-10-carbonyl)hydrazine.

3. As in claim 1, the compound which is 1-heptanoyl-2-(8-chloro-10,11-dihydrodibenz[b,f][1,4]oxazepine-10-carbonyl)hydrazine.

4. As in claim 1, the compound which is 1-decanoyl-2-(8-chloro-10,11-dihydrodibenz[b,f][1,4]oxazepine-10-carbonyl)hydrazine.

* * * * *